US008910918B2

(12) United States Patent
Gay et al.

(10) Patent No.: US 8,910,918 B2
(45) Date of Patent: Dec. 16, 2014

(54) CUTTING A COLLAPSIBLE TUBE FOR BIOPHARMACEUTICAL USE

(75) Inventors: Isabelle Valerie Christine Gay, Peypin (FR); Michael Bates, Gloucestershire (GB); Ray Bassett, Gloucestershire (GB); Chris Biddel, Gloucestershire (GB)

(73) Assignee: Sartorius Stedim FMT SAS, Aubagne (FR)

( * ) Notice: Subject to any disclaimer, the term of this patent is extended or adjusted under 35 U.S.C. 154(b) by 357 days.

(21) Appl. No.: 13/133,814

(22) PCT Filed: Nov. 24, 2009

(86) PCT No.: PCT/FR2009/052283
§ 371 (c)(1),
(2), (4) Date: Jul. 25, 2011

(87) PCT Pub. No.: WO2010/066977
PCT Pub. Date: Jun. 17, 2010

(65) Prior Publication Data
US 2012/0017733 A1    Jan. 26, 2012

(30) Foreign Application Priority Data

Dec. 10, 2008 (FR) ..................................... 08 06951

(51) Int. Cl.
*A61B 17/46* (2006.01)
*F16K 7/04* (2006.01)
*B26B 3/00* (2006.01)
*A61M 39/28* (2006.01)
*A61B 17/122* (2006.01)

(52) U.S. Cl.
CPC ...... *A61M 39/284* (2013.01); *A61B 2017/1225* (2013.01)
USPC ........ 251/9; 251/4; 30/124; 30/289; 606/120; 606/167

(58) Field of Classification Search
USPC .................. 251/4, 9; 29/243.5; 606/120, 167; 30/289, 290, 296.1, 298.4, 124, 92, 30/109, 113; 83/870, 762, 454, 932
See application file for complete search history.

(56) References Cited

U.S. PATENT DOCUMENTS 3,166,071 A * 1/1965 Mayer ........................... 606/120
3,323,208 A * 6/1967 Hurley, Jr. ..................... 606/120

(Continued)

FOREIGN PATENT DOCUMENTS

EP       0 799 627 A2    10/1997
WO    2005/117723 A2    12/2005

OTHER PUBLICATIONS

International Search Report, dated Jun. 1, 2010, from corresponding PCT application.

*Primary Examiner* — John K Fristoe, Jr.
*Assistant Examiner* — Daphne M Barry
(74) *Attorney, Agent, or Firm* — Young & Thompson (57) ABSTRACT

Process for closing and cutting into sections a flexible tube, with a cutting element and a pinching closing device for cutting into sections with two cross-sections, each with two parts with indentations that can be placed in removable extension by combination elements and that make a passage with an access, whereby the pinching closing device is in the open or closed state where the cross-sections are closed by locking members and where the surfaces form a pinching closing passage of the tube; the pinching region of the tube is positioned in the indentation of a cross-section; the other cross-section is brought opposite the preceding one and the pinching closing device in the closed state, with cooperation of the locking elements, the tube being positively pinched and closed in two positive pinching zones, and thus held in place; the tube is cut into sections between the parts in the closed state, using the cutting element by passing it into the passage without it interfering with the pinching closing device; and the parts are dissociated.

21 Claims, 5 Drawing Sheets

(56) References Cited

U.S. PATENT DOCUMENTS

| | | | |
|---|---|---|---|
| 4,026,294 A * | 5/1977 | Mattler | 606/120 |
| 4,429,852 A | 2/1984 | Tersteegen et al. | |
| 4,688,753 A * | 8/1987 | Tseng et al. | 251/7 |
| 4,716,886 A * | 1/1988 | Schulman et al. | 606/120 |
| 5,676,672 A * | 10/1997 | Watson et al. | 606/120 |
| 5,925,052 A | 7/1999 | Simmons | |
| 6,638,282 B2 * | 10/2003 | Ramsey et al. | 606/120 |
| 7,350,761 B1 * | 4/2008 | Stuart | 251/10 |
| 7,410,155 B2 | 8/2008 | Spain, III | |
| 2006/0145105 A1 * | 7/2006 | Ishida et al. | 251/7 |

* cited by examiner

CUTTING A COLLAPSIBLE TUBE FOR BIOPHARMACEUTICAL USE

The invention relates to cutting into sections a flexible tube as is typically intended for biopharmaceutical applications. Its purpose is more specially a process for closing and cutting into sections a flexible tube in a pinching region, a pinching closing device for cutting into sections, and a cutting element, specially intended to work with and form a pinching closing unit for cutting into sections that can implement the process.

A tube such as the one to which the invention applies makes possible the circulation, the passage, and the communication of a fluid, such as a biopharmaceutical fluid. For example, such a tube is inserted between two—or more—pockets.

Such a tube, usually having a circular cross-section, is typically made of plastic material such as silicone, but also PVC, with the list not being limiting. It exhibits a certain overall behavior and, at the same time, both a certain flexibility of the unit and a certain local flexibility, which makes it possible, by means of exerting enough pinching force, to pinch the tube by flattening it and crushing it to close it on itself.

In a typical embodiment, for example, the tube has an outside diameter of between, for example, 8 millimeters and 30 millimeters, whereby the thickness depends on material, diameter, and applications.

Most often, such a tube either is part of a device that comprises one or more pockets or functional means (filtration, mixing, . . . ) or is mounted on, and functionally combined with, a processing apparatus or device (sampling, circulation, . . . ).

Most often, the operations that relate to such tubes—and in particular cutting them into sections—have to be aseptic, i.e., their bacterial integrity should not be challenged.

In a certain number of cases, the process that involves the fluid that is channeled by the tube at one time or another requires that the tube be closed and cut into sections in a given region so as to prevent the circulation, the passage, and the communication of fluid on either side of this region and to be able to have separately two portions of the tube that is thus closed and cut into sections and that is adjacent to it, such as a pocket, a filter or other functional means.

The document U.S. Pat. No. 5,925,052 describes a device for cutting into sections and pinching end parts that are cut into sections of an umbilical cord, comprising a hand tool forming a clamp that is arranged to be manipulated by an operator, intended to accommodate in a removable way an individual unit that includes a pair of clamp supports and a cutting surface that is placed between them. The pair of clamp supports is intended in turn to accommodate two separate distinct clamps whose jaws comprise indentations equipped with teeth that are inscribed in a flat casing. The umbilical cord that is to be cut into sections can be placed between the two jaws of the two clamps. These two jaws are equipped with locking means such that once the jaws are closed, they remain closed. The first jaw of each clamp is intended to rest on the corresponding clamp support, itself intended to rest on the first jaw of the hand tool. The second jaw of each clamp, articulated on the first jaw, is moved by a journal that is carried by the second jaw of the hand tool, which is equipped with a cutting blade that is intended to work with the cutting surface of the individual unit that includes a pair of clamp supports and that for this purpose passes between the second two jaws of the two clamps.

Such a device has several limitations and drawbacks. First of all, it is specially suitable for cutting an umbilical cord into sections and not a tube such as the one that is involved here. Next, it requires a hand tool that forms a clamp that has a handle acting as a lever for the jaws. The pinching and the cutting into sections are necessarily concomitant. The use of hinged clamps does not allow a uniform compression of the umbilical cord. The pinching is achieved by a flat compression that most often is a source of leaks. The device is not truly suited to umbilical cords of different geometries. The two clamps and the two clamp supports are separated far from one another so as to make it possible to accommodate—between them—the cutting surface, which is located in the same plane as the casing of indentations of the jaws located on the same side. It follows that the cutting of the umbilical cord cannot be done from one side to the other of the two clamps.

The document EP-A-0 799 627 describes a device for pinching and cutting into sections that is derived from clamps used in the biopharmaceutical field and known under the name of Halkey clamps or Roberts clamps or else Halkey-Roberts clamps. The device combines a cutting blade with such a clamp. Such a device has the same drawbacks as those mentioned in relation to the document U.S. Pat. No. 5,925,052.

The document U.S. Pat. No. 7,410,155 describes a process for pinching and cutting a deformable tube that is intended for biopharmaceutical applications and a device for pinching such a tube. According to the process that is described in this document, there is a tube between the first and second cross-sections that are articulated with one another by a pinching device, with each cross-section having two articulated parts between them. Then, by a relative rotary movement for closing the first and second cross-sections, they are closed on one another, and the tube is pinched by flattening it between the two pairs of parts of the pinching device. The reciprocal-locking means of the two parts of each pair of parts of the first and second cross-sections are made to cooperate to keep them closed and to keep the tube pinched. Then, the tube is cut between the two pairs of parts of the device and at least one part of the first and second cross-sections, so as to form two separate tube lengths, each pinched at its cut end part. Thanks to the cooperation of the locking means, each pair of parts of the pinching device that is pinched over the corresponding length of the tube is held in place at least temporarily once the pinching device cut in two parts. Such a pinching device comprises a first cross-section and a second cross-section that are articulated with one another, with each cross-section itself having two parts articulated with one another. The first and the second cross-sections are arranged in such a way as to be able to be moved with pivoting in a way relative to one another between an open position and a closed position. The four parts comprise a hollow indentation with a flat bottom that comes over the tube on either side for pinching it. The device also comprises reciprocal locking means of the two parts of each pair of parts of the two cross-sections for keeping them at least temporarily in a closed position. Such a device is intended to be cut into sections to be able to cut the tube into sections.

Such a process and such a device have a number of drawbacks that are combined with one another. As above, the use of hinges does not allow uniform compression of the tube. The pinching is achieved by a flat compression with the inherent risk of leakage. The device is not suitable for tubes of different geometries (diameter and/or thickness). Cutting the tube into sections requires that of the device, which is an operation that is furthermore useless but nevertheless a source of drawbacks, whereby this cutting into sections can generate small troublesome pieces of the constituent material of the device.

The documents U.S. Pat. No. 5,676,672 and WO 2005/117723 describe devices for pinching and cutting into sections an umbilical cord, in which a cutting blade strikes a part of the device on which the umbilical cord rests. Such devices also have several limitations and drawbacks. They are specially suitable for cutting into sections an umbilical cord and not a tube such as the one involved here. The presence of hinges does not make possible a uniform compression of the umbilical cord. The pinching is achieved by a flat compression, a source of leaks.

The purpose of the invention is to eliminate limitations and drawbacks of the known processes and devices. Its purpose is to allow the pinching closing and the cutting into sections of a flexible tube that is intended for biopharmaceutical applications. It has as its object to remove the necessity for a hand tool such as a clamp. Its purpose is to allow an operation for cutting into sections that follows pinching. Its purpose is also a compression of the tube that is to be cut into sections that is uniform and a pinching without the risk of leakage and suitable for tubes of different geometries. Its purpose is also that the cutting of the tube can be done from one side to the other. Its purpose is also to avoid having to cut the device itself into sections and therefore to avoid small troublesome pieces of the constituent material of the device. Its purpose is to allow the tube, once it is cut into sections, from being closed permanently, and this by using the same pinching closing unit for cutting into sections. Its purpose is that this pinching closing unit for cutting into sections is a disposable unit and performs a function for permanently closing the tube on itself in the pinching region preventing any passage of fluid into the tube, which the devices according to the documents of the prior art do not allow. Actually, the requirement of a closing that prevents any passage of fluid into the tube is much more significant than the closing is permanent; in any case, its purpose is not to be reversible, whereby this requirement is less crucial in the case of a temporary and reversible closing.

The purpose of the invention is to propose such a pinching closing unit for cutting into sections that is inexpensive, easy to manufacture, and simple and reliable to use all at the same time. Actually, such a device should be able to be installed readily but effectively over the course of the process involving the fluid that is channeled by the tube.

For this purpose, according to a first aspect, the invention has as its object a process for cutting into sections and closing a flexible tube of the type in which:

There is a tube to be cut into sections and closed,
There is a pinching closing device for cutting into sections and at least one cutting element, with the pinching closing device for cutting into sections comprising two cross-sections, each having two hollow parts, at least one pair having indentations, whereby these hollow parts can be placed in the extension of one another by combination means while making between them a transverse passage for cutting into sections having an access that can allow the cutting element or a control element of the cutting element to pass, with the pinching closing device for cutting into sections able to be found either in the open state where the two cross-sections are separated from one another or in the closed state where they are drawn together and closed on one another and kept closed by locking means and where the surfaces of the indentations form a passage for pinching and closing the tube,
There is a pinching closing device for cutting into sections in the open state,
A pinching region of the tube is positioned in the indentation of a cross-section, and the other cross-section is brought opposite the preceding one and the pinching closing device for cutting into sections is brought into the closed state, with cooperation of the locking means, until the tube is positively pinched and closed in at least one positive pinching closing zone by the surfaces of the indentations, and the tube thus is kept pinched and closed between the cross-sections,
The tube is cut into sections between the parts of the pinching closing device for cutting into sections in the closed state, using at least one cutting element,
The combination means and therefore the parts of the pinching closing device are dissociated for cutting into sections, of which at least one pair of parts with indentations remains attached to the end part that is cut into sections of the tube by pinching it and by closing it.

This process is such that:
There is a pinching closing device for cutting into sections of which one of the indentations is a female indentation, and the other indentation is a male indentation, with the two indentations, in the closed state of the device, making between them a positive pinching closing passage that is limited by the two surfaces of the indentations, having, in the transverse straight cross-section, a general U shape,
And, for cutting the tube into sections, at least one cutting element is passed into the passage for cutting into sections without the cutting element cutting into sections, penetrating into, or interfering frontally with the pinching closing device for cutting into sections.

According to one option, the tube is cut into sections immediately after or a certain time after its positive pinching closing action has been implemented.

According to one option, the cutting element is passed into the passage for cutting into sections without contact with the pinching closing device for cutting into sections. According to another option, the cutting element is passed into the passage for cutting into sections with a sliding surface contact with the pinching closing device for cutting into sections.

As appropriate, the tube is cut into sections by means of a single cutting element or two opposite cutting elements.

According to one option, the tube is cut into sections in a flattening zone in which the tube is not pinched positively.

According to one option, one cross-section is brought opposite another, and the pinching closing device for cutting into sections is brought into the closed state by a relative movement of transverse translatory motion or pivoting around an axis that, relative to the longitudinal axis of the device, is offset on a longitudinal side of the device.

According to one option, the tube is kept positively pinched and closed in a single positive pinching closing zone, and the tube is held in place in another zone. According to another option, the tube is kept positively pinched and closed in two positive pinching closing zones.

According to a first option, the combination means and therefore the parts of the pinching closing device are dissociated, whereas only one of the pairs of parts with indentations is attached to the end part that is cut into sections of the tube by pinching it and by closing it. According to a second option, the combination means are dissociated whereas the two pairs of parts with indentations remain attached to the end part that is cut into sections of the tube by pinching it and by closing it.

According to one option, the pinching closing of the tube is begun in the zone of two lateral folds of the tube.

According to a second aspect, the invention has as its object a pinching closing device for cutting into sections that is specially intended, in combination with a cutting element, for the implementation of the process that was just described, which comprises two cross-sections, each having two hollow parts, at least one pair having indentations, whereby these parts can be placed in the extension of one another in a removable way by combination means while providing between them a transverse passage for cutting into sections having an access that can allow the cutting element or a control element of the cutting element to pass, whereby the pinching closing device for cutting into sections can be found either in the open state where the two cross-sections are separated from one another or in the closed state where they are drawn together and closed on one another and kept closed by locking means and where the surfaces of the indentations form a passage for pinching and closing the tube, comprising at least one segment to which a space is axially adjacent, in which space the passage empties and where the tube is, on the one hand, held in place, and, on the other hand, flattened to a certain degree, with one of the indentations being a female indentation, and with the other indentation being a male indentation, the two indentations, in the closed state of the pinching closing device for cutting into sections making between them a positive pinching closing passage that is limited by the two surfaces of the indentations, having, in a transverse straight cross-section, a general U shape.

According to one embodiment, the width of the opening of the pinching passage, defined by the transverse separation between the surfaces of the transverse straight cross-section in the general U shape, is slightly smaller than twice the thickness of the wall of the flexible tube to be pinched.

According to one embodiment, in a transverse straight cross-section, the male indentation has a general U shape with a core and two wings; in a transverse straight cross-section, the female indentation has a general U shape with a core and two wings; and in a transverse straight cross-section, the pinching passage has a general U shape with a core and two wings; the two wings opposite each pair of wings facing the male indentation and the female indentation, by drawing together toward their opposite ends, go to the cores of the indentations, at least in the zone of these ends, and each of the two wings of the pinching passage has, between the surfaces of the two indentations, an opening whose width will diminish towards its end that is opposite to the core of the pinching passage.

According to one embodiment, the cross-sections are contoured and extend along the longitudinal axis, whereby the positive pinching closing zone extends over a certain axial length.

According to one embodiment, the two hollow parts of each cross-section are analogous, with the pinching closing device for cutting into sections ensuring a function of the tube closing on itself in two positive pinching closing zones. In this case, the positive pinching closing passage is—in two positive pinching closing segments—placed in the extension of one another with a separation between them where the positive pinching closing passage is absent to the point where it does not exist.

According to another embodiment, the two hollow parts of each cross-section are different, with the pinching closing device for cutting into sections ensuring a function of closing the tube on itself in a single positive pinching closing zone and being held in place only in the other zone.

According to one embodiment, the locking means are irreversible for the two pairs of hollow parts. According to another embodiment, the locking means are irreversible for one of the pairs of hollow parts and reversible for the other. In particular, the locking means are reversible for one pair of hollow parts ensuring only a simple holding in place of the tube T.

According to one embodiment, the locking means are irreversible, such that the two cross-sections that are brought into the closed state are held in place in this state by locking means without being able to be dissociated, whereby these locking means comprise contoured hooking teeth, oriented in two opposite directions.

According to one embodiment, the pinching passage has an adjustable opening, with the relative movement for bringing one cross-section opposite another and the pinching closing device for cutting into sections in the closed state being more or less large so that the pinching passage is respectively more or less small.

According to one embodiment, the two indentations have the same shape, the same arrangement, and the same dimensions, constant and uniform, from one free end to the other. According to another embodiment, one and/or the other of the two indentations is slightly inclined along the axis of the pinching closing device for cutting into sections, toward the free border of the edge of the lip and toward the proximal end for exerting a more significant pinching of the tube toward the proximal end and for expelling the fluid that is found in the tube toward the distal end.

According to one embodiment, the transverse passage for cutting into sections is made between the two pairs of transverse end surfaces and proximal surfaces of the cross-sections, located opposite one another and offset close to one another along the axis of the pinching closing device for cutting into sections.

According to one embodiment, separation means that consist of stops made on the end surfaces and proximal surfaces or combination means are provided.

According to one embodiment, the combination means comprise at least one projection made on one of the parts of the device, able to work in a removable way with at least one blind hole, or hollow, or groove that is complementary, made on the other part of the same cross-section. For example, a projection and a hole or groove extends parallel to the axis or transversally.

According to another embodiment, the combination means comprise at least one removable connecting part in the form of a clip, able to combine the two parts in a removable way and in an indirect way, with the clip comprising a core from which four projections that are in rod form and that are able to work with four transverse grooves made on the outside surface of the pinching closing device for cutting into sections are adjacent, on each part.

According to another embodiment, the combination means comprise a cradle-shaped removable connecting part that can combine the two parts in a removable way and in an indirect way, with the cradle comprising two lips that face one another, able to encircle the parts by their distal end surfaces.

According to a first embodiment, the two cross-sections are two separate parts and are brought into the closed state by a relative transverse sliding movement.

In this embodiment, one of the two cross-sections is a male cross-section and the other is a female cross-section, whereby the male cross-section comprises and is limited on the outside by a first core and two first lips, with the female cross-section comprising and being limited on the outside by a second core and two second lips.

In this embodiment, the separation between the two opposite outside surfaces of the first two lips corresponds to the separation between the two inside surfaces opposite the second two lips, in such a way as to allow, in the closed state of the pinching closing device for cutting into sections, the interlocking with adjustment of the two cross-sections, with the pair of outside surfaces then being in contact and supported on the pair of inside surfaces.

According to one embodiment, the reciprocal-locking means are two units that comprise a series of teeth respectively made on the two outside surfaces of the first lips and the two inside surfaces of the second lips in their interlocking zone.

According to one embodiment, the male cross-section defines a female indentation, and the female cross-section defines a male indentation.

According to a second embodiment, the two cross-sections are two parts that are structurally combined with one another in pivoting around an axis that, relative to the longitudinal axis of the pinching closing device for cutting into sections, is offset on a longitudinal side of the device, with the two cross-sections being brought into the closed state by a relative pivoting movement around the pivoting axis.

In this embodiment, the reciprocal-locking means comprise teeth that are located on the side that is opposite to the pivoting axis. More specifically, the reciprocal-locking means comprise a female part that is connected to one of the parts and equipped with teeth and a male part that is connected to the other part and equipped with teeth.

According to one embodiment, the two cross-sections have the same axial length.

According to a third aspect, the invention has as its object a cutting element that is specially intended, in combination with a pinching closing device, for cutting into sections for the implementation of the process described above, such that its shape and its dimensions are selected in such a way that the cutting element can—via an access—pass into a transverse passage for cutting into sections the pinching closing device for cutting into sections and thus can cut into sections the tube that is pinched and closed by this device.

According to a fourth aspect, the invention has as its object a pinching closing unit for cutting into sections that comprises a pinching closing device for cutting into sections as described above and at least one cutting element as described above, whereby the cutting element is able to pass into the passage for cutting into sections without it cutting into sections, penetrating into, or interfering frontally with the pinching closing device for cutting into sections.

According to a first production of such a unit, the pinching closing device for cutting into sections structurally and functionally includes at least one cutting element.

In this embodiment, the cutting element can be mounted to slide in its own plane on the proximal end surface of one of the parts.

According to a second embodiment, the pinching closing device for cutting into sections does not structurally include at the least one cutting element, the latter being combined functionally with it.

Several embodiments of the invention are now described using drawings in which.

A pinching closing unit for cutting into sections comprises a device 1 that makes it possible to ensure a pinching closing of a tube T as defined above, in the desired region, functionally combined with at least one cutting element 2, integrated or outside of the one that makes it possible to ensure the transverse cutting into sections of the tube T.

Once the pinching closing device 1 for cutting into sections has been implemented to ensure the positive pinching closing of the tube T and its transverse cutting into sections by means of the cutting element 2, the purpose of the pinching closing device 1 for cutting into sections is to remain attached to the tube T.

The unit 1+2, as the pinching closing device 1 for cutting into sections, can be referred to as a disposable unit or device.

Figure 1:
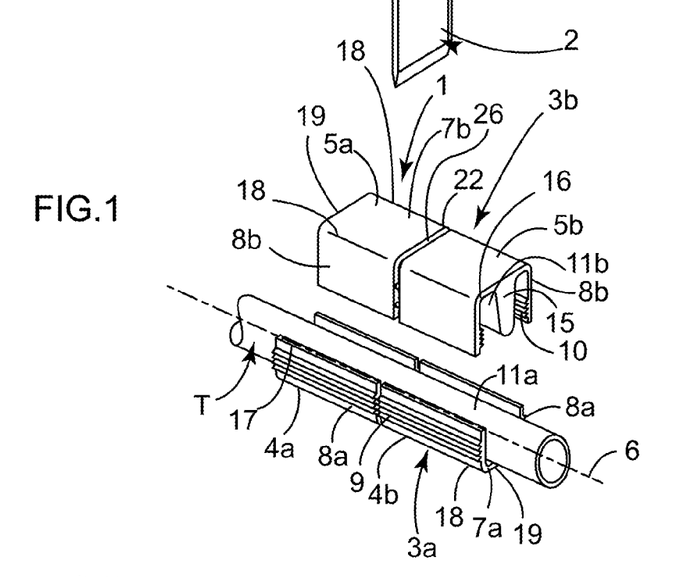
FIG. 1 is a perspective view of a first possible embodiment family of a pinching closing unit for cutting into sections in the open state, with a portion of the tube in position, a cutting element being shown diagrammatically.

FIG. 1 illustrates a unit that comprises a pinching closing device 1 for cutting into sections including two cross-sections 3, hollow, contoured, namely a first male cross-section 3a and a second female cross-section 3b.

Each cross-section 3a, 3b comprises two parts that are likewise hollow and contoured, namely, respectively, the two parts 4a and 4b for the male cross-section 3a and the two parts 5a and 5b for the female cross-section 3b.

The two cross-sections 3a and 3b are able, based on the operating phases, to be structurally and functionally associated with one another by a normally irreversible interlocking for forming a rigid unit, whereby the two hollow parts are opposite (FIG. 2) (pinching phase, phase for cutting into sections) or to be dissociated (FIG. 1) (installation phase).

The two parts 4a and 4b or 5a and 5b of the same cross-section 3a or 3b are able, according to the operating phases, to be structurally and functionally combined with one another by being placed in the extension of one another (FIG. 1) (pinching phase, phase for cutting into sections) or to be dissociated (FIGS. 4, 5, and 6) (dissociation phase).

When the two cross-sections 3a and 3b are structurally and functionally combined with one another by interlocking, their respective opposite parts 4a and 5a, on the one hand, and 4b and 5b, on the other hand, are also structurally and functionally combined with one another by an interlocking that, under the normal conditions of use, is irreversible.

The cross-sections are generically referenced 3 and the parts 4 and 5.

The pinching closing device 1 for cutting into sections therefore comprises the four separate parts 4a, 4b, 5a and 5b that are compact, contoured, rigid and typically made of plastic material such as a polymer that is selected for satisfying, if necessary, the other constraints that the pinching closing device 1 for cutting into sections has to face, for example, to withstand treatment in an autoclave or by γ-radiation.

In one embodiment, the parts 4a and 4b of the cross-section 3a are, if not strictly identical, at least analogous with one another, likewise regarding the parts 5a and 5b of the cross-section 3b. In this case, the pinching closing device 1 for cutting into sections ensures a function for closing the tube T on itself in two positive pinching closing zones.

However, in another embodiment, the two hollow parts 4a, 4b and 5a, 5b are not analogous, but different, in such a way that, for example, the pinching closing device 1 for cutting into sections ensures a closing function of the tube T on itself only in a single positive pinching closing zone. In its other zone, the tube T is then simply held in place, which facilitates its transverse cutting into sections. If necessary, this holding in place can be removed, existing only as necessary for cutting into sections.

The pinching closing device 1 for cutting into sections has a longitudinal axis 6 that is also the longitudinal axis of the tube T when the latter is placed in the pinching closing device 1 for cutting into sections. This is in relation to this axis 6 that describes as "axial" any direction or plane that extends parallel to the axis 6 and as "transverse" any direction or plane that extends orthogonally to the axis 6.

The two cross-sections 3a and 3b are contoured and extend along the axis 6.

In the embodiment shown, the two cross-sections 3a and 3b are one-piece and of the same axial length in such a way as to be able to be interlocked by being adjusted opposite one another.

Each of the two cross-sections 3a and 3b, or each of its two parts 4a, 4b and 5a, 5b, has an outside contour that has a general U shape in a transverse, straight cross-section. This contour comprises and is limited by several segments, namely a core and, on either side of the latter, two lateral lips, whereby the core and the two lips furthermore extend axially.

"General U shape" is defined as a shape that is defined by a median core and two lateral wings on either side, opposite one another and extending in the same general common direction.

The first male cross-section 3a comprises and is limited on the outside by a first core 7a and two first lips 8a. The second female cross-section 3b comprises and is limited on the outside by a second core 7b and two second lips 8b.

The separation between the two opposite outside surfaces 9 of the first two lips 8a corresponds to the separation between the two inside surfaces 10 opposite the second two lips 8b. This arrangement makes possible, in the closed state of the pinching closing device 1 for cutting into sections, the interlocking with adjustment of the two cross-sections 3a and 3b, or their constituent parts, whereby the pair of outside surfaces 9 is then in contact and supported on the pair of inside surfaces 10.

In the embodiment shown, the first male cross-section 3a defines a first female indentation 11a, and the second female cross-section 3b defines a second male indentation 11b.

Figure 8:
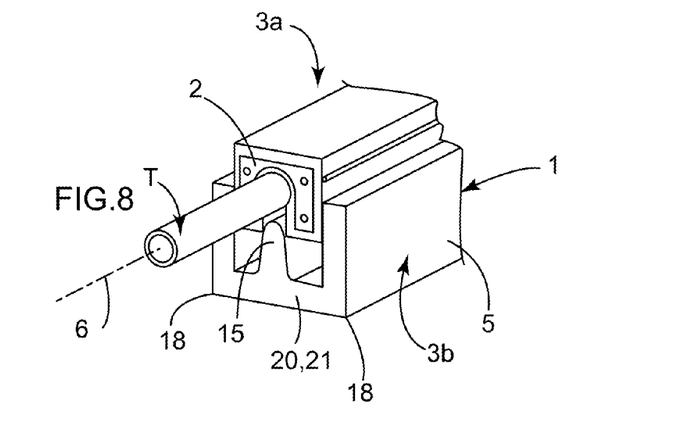
FIG. 8 is a perspective view of another possible embodiment of the cutting element combined with a pinching closing unit for cutting into sections that is partially shown.

According to another embodiment, the arrangement is reversed, with the first male cross-section 3a defining a first male indentation and the second female cross-section 3b defining a second female indentation (FIG. 8).

The first female indentation 11a is defined by a contoured surface 13, extending along the axis 6, having—in the transverse cross-section—a contour of the soffit of a U and extending parallel to the axis 6. The surface 13 consists of the inside surface 35 of the first core 7a, arranged in a median way, and two inside surfaces 36a and 36b of the first two lips 8a, arranged laterally on either side of the inside surface 35. Thus, the female indentation 11a comprises a core 35 and two wings 36a and 36b.

The second male indentation 11b is defined by a contoured surface 14, extending along the axis 6, having—in the transverse cross-section—a contour of the extrados of a U and extending parallel to the axis 6. The surface 14 consists of the outside surface 37 of the end part of a projection 15, arranged in a median way, and two outside surfaces 38a and 38b of the body of the projection 15, placed on either side of the outside surface 37. Thus, the male indentation 11b comprises a core 37 and two wings 38a and 38b.

The projection 15 is adjacent to the second core 7b and extends at an equal distance between the second two lips 8b by being directed in the same direction as they are.

The surface 14 is connected to the two inside surfaces 10 of the two lips 8b by two small, essentially coplanar surfaces 16. These two small surfaces 16 are able, if necessary, when the interlocking of the two cross-sections 3a and 3b is the largest, to be in contact and supported on the two free edges 17 of the two lips 8a, in the closed state of the pinching closing device 1 for cutting into sections.

Of course, to be able to implement the required interlocking, the two surfaces 13 and 14 are arranged head-to-foot relative to one another. If one is arranged in a U (upright U), the other is arranged in a ∩ (inverted U).

The surfaces 13 and 14 are mated in such a way as to be able to work together and to ensure the pinching of the tube T on itself until it is totally closed, whereby the cores 35 and 36 are mated together, just as, on the one hand, the wings 36a and 38a, and, on the other hand, the wings 36b and 38b. Like the indentations 11a, 11b, the pinching extends along the axis 6, i.e., it is not specific, but linear over a certain length.

The surfaces 13 and 14 are smooth overall. In the embodiment shown, the surfaces 13 and 14 have simple shapes and not distorted shapes.

In the embodiment shown, the cores 35 and 37 have an overall flattened shape with a slight curve, respectively concave and convex. The wings 36a, 36b, 38a, 38b have an overall flattened shape.

The two wings 36a and 36b of the pair of wings 36a, 36b of the female indentation 11a diverge slightly from the core 35 in such a way that the opening of the female indentation 11b is slightly tapered. These wings 36a and 36b are connected to the core 35 by two rounded parts 39 with a fairly large radius of curvature.

The two wings 38a and 38b of the pair of wings 38a, 38b of the male indentation 11b are slightly convergent from the second core 7b that constitutes the base of the projection 15. These wings 38a and 38b are connected to the core 37 by two rounded parts 40 with a fairly large radius of curvature.

The surfaces 13 and 14 have overall analogous contours, as it is described. They are intended to be arranged as a whole in the same direction. They are offset transversely from one another as a result of the presence between them of the tube T that is positively pinched and closed because of the geometry that they exhibit. They are thus held in place thanks to locking means, which will be referenced again.

The pinching closing device 1 for cutting into sections and its constituent parts (cross-sections 3 and parts 4 and 5) can be found in one of the following two states: open state and closed state.

In the open state (FIG. 1), the two cross-sections 3a and 3b are separated and dissociated from one another. The two cross-sections 3a and 3b can then be manipulated, each one separately. In this open state, the two cross-sections 3a and 3b allow a free access that is transversal to the indentations 11a and 11b, each of them not being covered by the cross-section to which the other indentation belongs.

In the open state, the tube T can, in any longitudinal region that is desired for being a pinching region RP, be introduced into—or if necessary removed from—the female indentation 11a that forms a cradle, without its shape being affected, in particular if it is pinched or flattened, with the circulation, the passage for cutting into sections, the communication of the fluid into the tube T not being blocked, prevented, or impeded. The cradle of the female indentation 11a is, of course, matched to the shape and to the transverse dimension of the tube T.

Thus, the open state makes possible the installation phase of the tube T in the pinching closing device 1 for cutting into sections, optionally its removal (FIG. 1).

In the closed state (FIGS. 3, 3A), the two cross-sections 3a and 3b are close to one another and interlocked, with the two lips 8a of the first male cross-section 3a being housed with holding contact, in the two lips 8b of the second female cross-section 3b.

Figure 3:
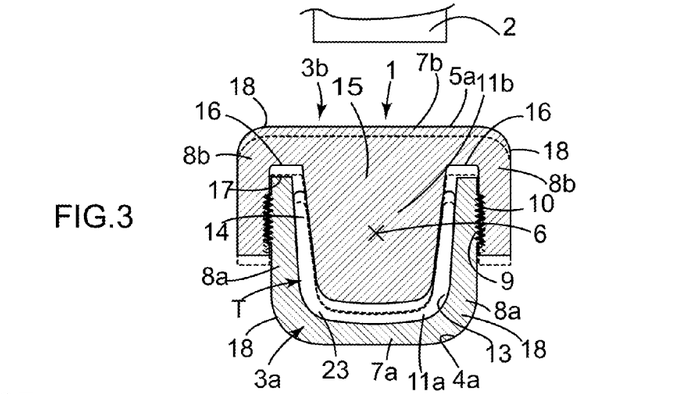
FIG. 3 is a transverse cutaway view of a pinching closing unit for cutting into sections in the closed state, with a portion of the tube in position.
Figure 3A:
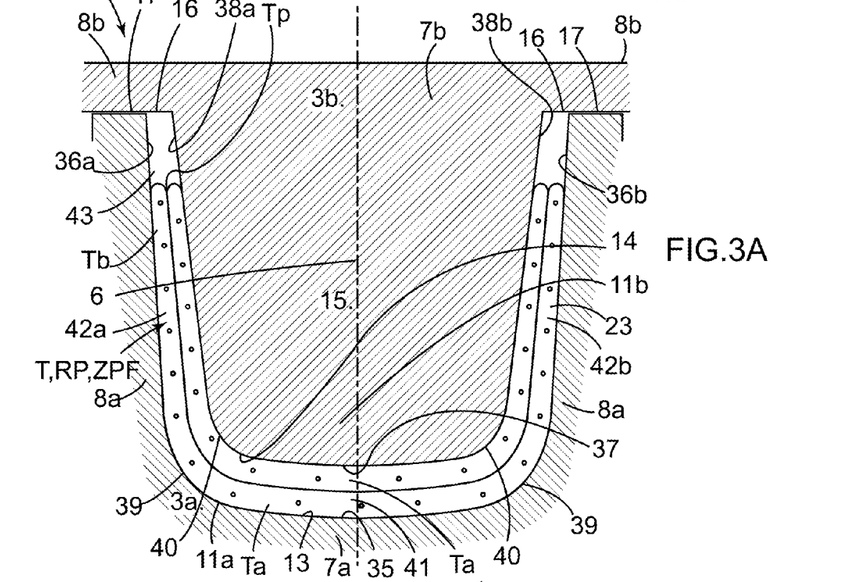
FIG. 3A is a larger-scale partial view of FIG. 3.

In the closed state, the two outside surfaces 9 of the first lips 8a are in contact and supported on the two inside surfaces 10 of the second lips 8b, and, if necessary—as indicated above—the two small surfaces 16 are in contact and supported on the two free edges 17 of the second lips 8b.

In the closed state, the pinching closing device 1 for cutting into sections has a general outside shape that is essentially that of a parallelepiped with an at least essentially square transverse cross-section, elongated along the axis 6, and whose four edges 18 that extend axially are rounded. This parallelepiped comprises two free ends or transverse end surfaces and distal surfaces 19 (FIG. 4).

Figure 4:
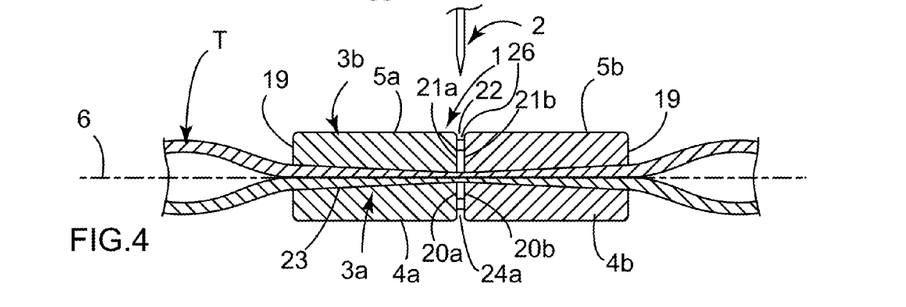
FIG. 4 is a longitudinal cutaway view of a possible embodiment of a pinching closing unit for cutting into sections in the closed state, with a portion of the tube in position.
Figures 5, 6, 7:
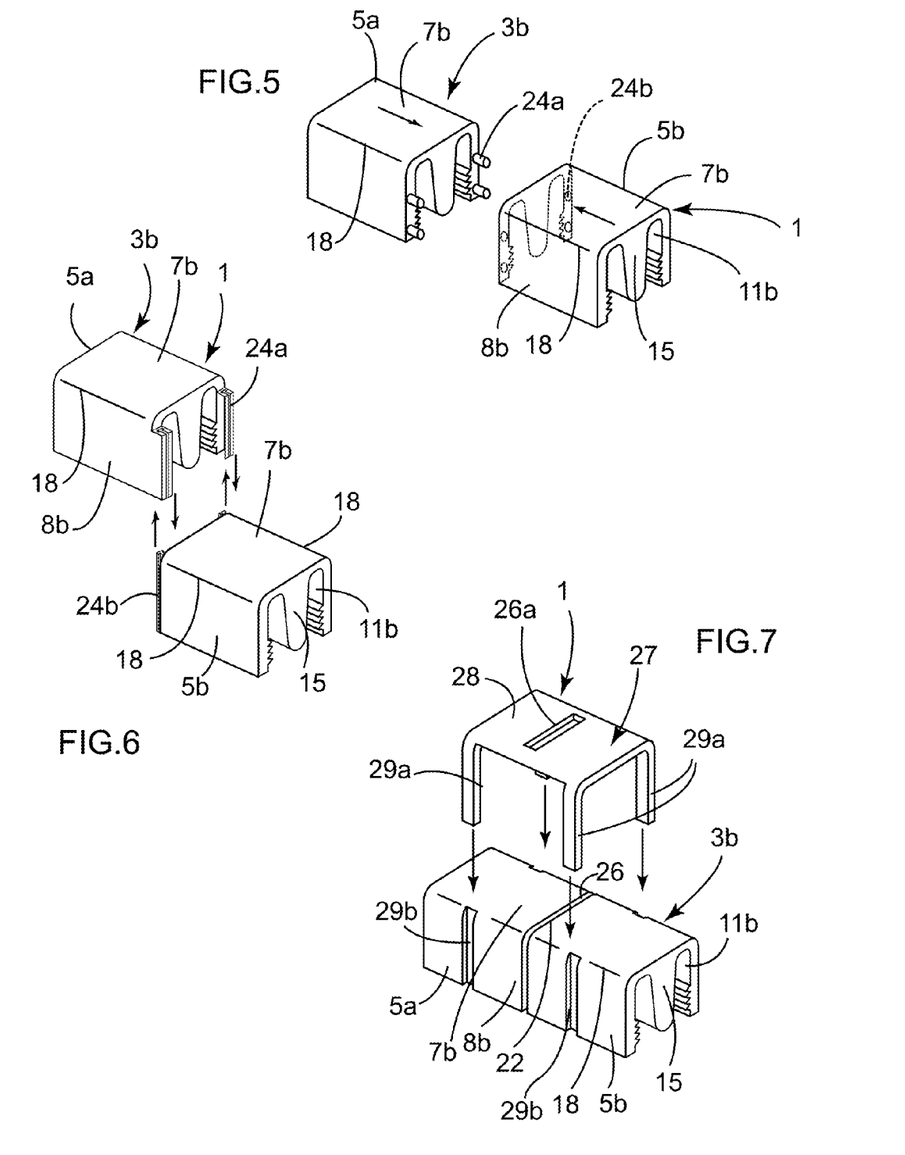
FIGS. 5, 6 and 7 are three perspective views of three possible embodiments of locking means of a pinching closing unit for cutting into sections that is partially shown.

Each of the parts 4a, 4b, 5a, 5b is terminated from the exterior side by a free end or transverse distal end surface 19 and from the interior side by transverse end surfaces and proximal surfaces, namely, respectively, 20a, 20b, 21a, 21b (FIGS. 4 and 5). These transverse end surfaces and proximal surfaces are essentially planar.

In the closed state, the two parts 4a and 4b, 5a and 5b of each of the two cross-sections 3a and 3b have their two transverse end surfaces and proximal surfaces 20a and 20b, 21a and 21b located opposite one another and in the immediate proximity of one another but nevertheless offset from one another, along the longitudinal axis 6, in such a way as to make a median transverse passage for cutting into sections 22. The two transverse end surfaces and proximal surfaces 20a and 21a of the parts 4a and 5a, like the two transverse end surfaces and proximal surfaces 20b and 21b of the parts 4b and 5b, are coplanar or essentially coplanar.

In the closed state, the two indentations 11a and 11b no longer have free transverse access as in the open state, but between them they make a positive pinching closing passage 23, with an axis 6, forming a type of hollow channel, limited by the two surfaces 13 and 14 of the indentations 11a and 11b, and the part of the small surfaces 16 that are adjacent to the projection 15.

In this embodiment, the positive pinching closing passage 23 is in two positive pinching closing segments 23a that are placed in the line of extension of one another. These two segments 23a first come out from the two transverse end surfaces and distal surfaces 19 to the outside of the pinching closing device 1 for cutting into sections. These two segments 23a next come out from the two pairs of transverse end surfaces and proximal surfaces 20a, 21a and 20b, 21b.

Between the two pairs of transverse end surfaces and proximal surfaces 20a, 21a and 20b, 21b, the positive pinching closing passage 23 is absent to the point where it does not exist, with the pairs of parts 4a, 5a and 4b, 5b being offset from one another in the axial direction, over a small distance, as indicated above.

The two positive pinching closing segments 23a are therefore placed in the extension of one another but with a small separation between them 23b.

Figure 2:
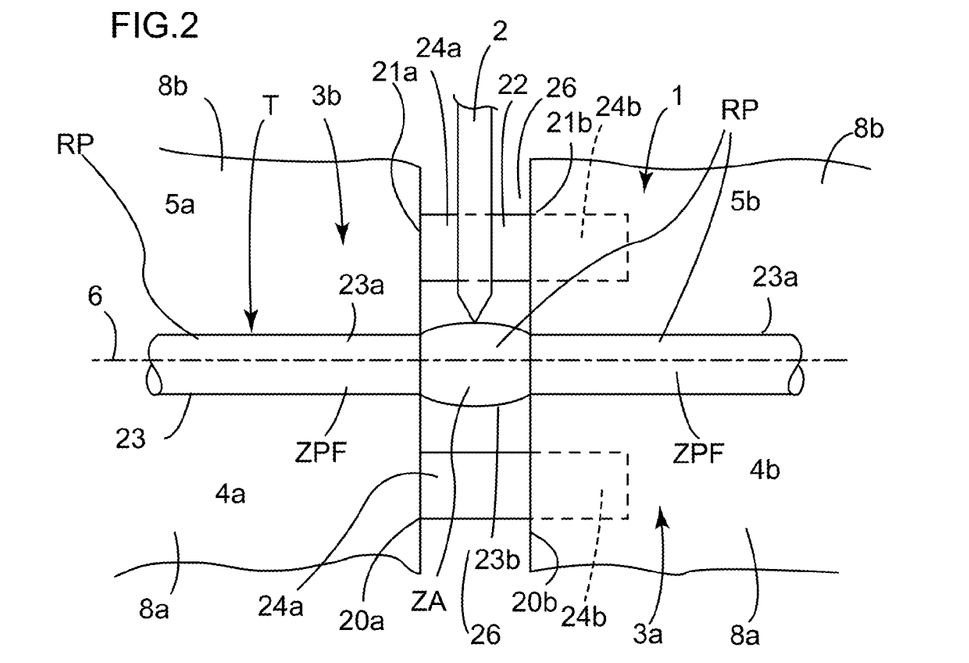
FIG. 2 is a partial, axial cutaway view, on a larger scale, of a pinching closing unit for cutting into sections and a portion of the tube in position, just before the beginning of cutting the tube into sections.

By referring to FIG. 2, "positive pinching closing zone" ZPF of the tube T is conventionally called the longitudinal segment of the tube T that is to the right of the parts 4a and 5a, 4b and 5b of the pinching closing device 1 for cutting into sections, in the two positive pinching closing segments 23a of passage 23. "Flattening zone" ZA of the tube T is called the longitudinal section of the tube T that is between the parts 4a and 5a, 4b and 5b of the pinching closing device 1 for cutting into sections, in the separation 23b between the two segments 23a of the passage 23. The pinching region RP of the tube T, already mentioned, consists of the longitudinal segment of the tube T that comprises the two positive pinching closing zones ZPF and the flattening zone ZA that is placed between them.

In one embodiment, the parts 4a and 4b, on the one hand, and 5a and 5b, on the other hand, are analogous, in such a way that the pinching closing device 1 for cutting into sections ensures a closing function of the tube T on itself in the two positive pinching closing zones ZPF, extending over a certain axial length, separated from one another by the flattening zone ZA. In this zone, the tube T is held in place without a total closing being positively ensured. Holding the tube T in place facilitates its cutting into sections.

In another embodiment, it is possible to provide that the pinching closing device 1 for cutting into sections ensures a closing function of the tube T on itself in a single positive pinching closing zone ZPF. In the preceding embodiment, this which was the other positive pinching closing zone ZPF can only ensure the positive holding in place, without total closing, with the flattening zone ZA then playing the same role as in the preceding embodiment. In this case, it is essential that the hollow parts ensuring this simple positive holding in place comprise indentations such as those described above.

The pinching passage 23, in the transverse straight cross-section, has a general U shape, as a result of the corresponding shape of the indentations 11a, 11b. This passage 23 consequently comprises a core 41 and two wings 42a and 42b, respectively corresponding to the cores 35 and 37 and to the wings 36a, 38a and 36b, 38b.

The tube T that is arranged in the pinching passage 23 of the pinching closing device 1 for cutting into sections in the closed state, constrained by the contoured passage 23, is formed by being, on the one hand, flattened on itself and thus closed, and, on the other hand, shaped in a U, with a core Ta and two wings Tb, terminated by two end folds Tp.

The width (in a transverse plane) of the opening that forms the pinching passage 23—core 41 and wings 42a and 42b—is defined by the transverse separation between the inside surface 13 and the surface 14, namely the transverse separation between the cores 35 and 37, on the one hand, and the wings opposite the pairs of wings 36a and 38a, 36b and 38b.

In the closed state, the two wings 36a and 38a, 36b and 38b of each pair of wings opposite the male indentation 11a and the female indentation 11b will draw together toward their ends 43 that are opposite the cores 35 and 37 of the indentations, at least in the zone of these ends 43. The cross-sections 3a and 3b are arranged accordingly.

In the embodiment shown, the two wings 36a and 38a, 36b and 38b will draw together in a more or less continuous way from the cores 35 and 37 to the opposite ends 43.

As a result, each of the two wings 42a and 42b of the passage 23 has—between the surfaces 36a, 38a and 36b, 38b of the two indentations—an opening whose width will diminish toward its end that is opposite to the core 41 of the passage 23, and in particular will diminish more or less continuously from the core 41.

The greatest width of the passage 23 is slightly smaller than twice the thickness of the wall of the tube T, based on the compressibility of the tube T, in such a way that the tube T—once placed in the pinching closing device 1 for cutting into sections in the closed state—is compressed on itself, and the pinching closing device 1 for cutting into sections ensures a closing function of the tube T on itself.

As a consequence of the fact that the width of the passage 23 will diminish, toward its end opposite the core 41, the tube T is more heavily compressed in the zone of its two folds Tp. This arrangement makes it possible to prevent a small opening of the tube on itself from persisting in the zone of folds since such an opening has the effect of allowing one or more drops of fluid of the tube T to flow from it during the pinching closing and the cutting of the tube T into sections.

Thus, the pinching closing device 1 for cutting into pinching sections performs a function of closing the tube T on itself in the pinching region, preventing any passage of the fluid into the tube T.

Once the tube T, in the installation phase, positioned in the female indentation 11a, whereas the pinching closing device 1 for cutting into sections is in the open state, the pinching closing device 1 for cutting into sections is brought into the closed state; the tube T is clasped in the passage 23 in the pinching phase.

In the pinching phase, the tube T is positively pinched and closed in its two positive pinching closing zones ZPF by the surfaces 13 and 14 and the cooperation of the indentations 11a and 11b. Between the two positive pinching closing zones ZPF, the tube T is not positively pinched and closed, but it is flattened more or less significantly to a certain degree, which justifies that this segment of the tube T is referred to as flattening zone ZA. As a result of the positive pinching closing, the tube T is closed on itself in the pinching region RP, which prevents the circulation, the passage, and the communication of fluid on either side of this region.

With at least one cutting element 2, the tube T is, in a phase for cutting into sections that follows the pinching phase, cut into sections transversely in the passage for cutting into sections 22, in the flattening zone ZA, and therefore in the pinching region RP. With the cutting into sections taking place after the closing, it is in no way disturbed by the fluid that is found in the tube T. With the closing being total, the risk that one or more drops of fluid will flow from the tube T is avoided.

The shapes and dimensions of the pinching closing device 1 for cutting into sections are adapted to the nature, the shape and the dimensions of tube T, in such a way that the desired pinching closing relative to the tube T is correctly achieved.

On the other hand, the shape and the dimensions of the cutting element 2 are selected in such a way that the cutting element 2 can—via the access 26—pass into the transverse passage for cutting into sections 22 from the pinching closing device 1 for cutting into sections and thus can cut into sections the tube that is pinched and closed by this device 1.

In the embodiment of FIG. 1, the female indentation 11a and the male indentation 11b have the same shape, the same arrangement and the same dimensions, constant and uniform, from one free and distal end 19 to the other free and distal end 19, via the proximal ends.

So as to be able to be placed and held in place in the extension of one another (FIG. 1), the two parts 4a and 4b or 5a and 5b of the same cross-section 3a or 3b are structurally and functionally combined with one another, in a removable way, by combination means.

More specially, the two parts 4a and 4b or 5a and 5b are combined by their end and proximal surfaces, respectively 20a and 20b, on the one hand, and 21a and 21b, on the other hand (separated along the axis 6 for forming the passage for cutting into sections 22), thanks to combination means 24a and 24b that belong to the parts 4a and 4b, on the one hand, and 5a and 5b, on the other hand.

In the embodiment of FIGS. 1 and 5, the combination means 24 comprise several (here, four, but the number can be different) projections or lugs that form studs 24a that are made on the end surfaces and proximal surfaces 20a, 20b, 21a, 21b of one of the two parts 4a, 4b, 5a, 5b, able to cooperate in a removable way with a number that is equal to blind holes or hollows forming cavities 24b, complementary, made on the end surfaces and proximal surfaces 20b, 20a, 21b, 21a of the other of the two parts 4b, 4a, 5b, 5a.

These projections 24a and these holes 24b extend parallel to the axis 6 and therefore to the direction of extension of the tube T when it is positioned in the pinching closing device 1 for cutting into sections. Their cooperation is achieved by an axial sliding parallel to the axis 6. Their dimensions are such that the projections 24a are housed with minimal play in the holes 24b.

So that the holding in place of parts 4a and 4b, on the one hand, and 5a and 5b, on the other hand, is ensured in an effective way, the projection 24a and the holes 24b are arranged in pairs of lips 8a, on the one hand, and 8b, on the other hand, on either side of the indentations 11a and 11b and of the passage for cutting into sections 22.

So as not to obstruct the access and the opening of the passage for cutting into sections 22, it is provided that no projection and no hole such as 24a, 24b is to the right of cores 7a and 7b.

According to other embodiments, the number of projections 24a and holes 24b is different, or—on the same given end surfaces and proximal surfaces 20a, 20b, 21a, 21b—not one or more projections 24a or holes 24b, but rather a combination of projections 24a and holes 24b is/are provided.

The transverse passage for cutting into sections 22 is produced by the presence of separation means that are provided to this end. These separation means consist of stops provided either on the end surfaces and proximal surfaces 20a, 20b, 21a, 21b or on the combination means 24a, 24b; for example, the projections 24a are locked at the end of travel in the holes 24b.

In the embodiment of the pinching closing device 1 for cutting into sections that is shown in FIG. 1, the two cross-sections 3a and 3b comprise reciprocal-locking means 25a and 25b of the two cross-sections 3a and 3b and parts 4a and 5a in the closed state. These locking means 25a and 25b are irreversible, with the two cross-sections 3a and 3b once brought to the closed state being held in place in this state by the locking means 25a and 25b, without being able to be dissociated.

Thus, once the tube T that is housed in the passage 23 has been pinched and closed, with the pinching closing device 1 for cutting into sections having been brought to the closed state, the tube T is thus held in place pinched and closed, and it remains in this state, with the pinching closing device 1 for cutting into sections being combined with the tube T as a result of the irreversibility of the locking means 25a and 25b.

In the embodiment of the pinching closing unit for cutting into sections that is shown in FIG. 1, in which the positive pinching closing takes place in two positive pinching closing zones ZPF, the two cross-sections 3a and 3b comprise reciprocal-locking means 25a and 25b of the two cross-sections 3a and 3b and two pairs of parts 4a, 5a and 4b, 5b in the closed state.

In one variant of this embodiment, the irreversibility of the locking means 25a and 25b is provided for only one of the two pairs of parts 4a, 5a and 4b, 5b. This variant is useful when it is desired that one end for cutting into sections is closed without the necessity that the other end for cutting into sections also be closed, with the corresponding parts of the cross-sections 3a and 3b then being able to be removed.

In another embodiment of a pinching closing unit for cutting into sections where the pinching closing device 1 for cutting into sections ensures a closing function of the tube T on itself in a single positive pinching closing zone ZPF, with the other zone ensuring only a holding in place without total closing, it is also possible to provide that the irreversibility of the locking means 25a and 25b is provided only for the parts of cross-sections 3a and 3b that ensure the positive pinching closing, but is not provided for the parts that ensure only a holding in place without total closing.

In the embodiment of FIGS. 1 and 5, the reciprocal-locking means 25a and 25b are two units that comprise a series of contoured, irreversible hooking teeth (or catches), oriented in two opposite directions, extending axially, made respectively on the two outside surfaces 9 of the first lips 8a and the two inside surfaces 10 of the second lips 8b in their interlocking zone.

Instead of teeth, it is possible to provide catches or the like.

In the embodiment of FIGS. 1, 3 and 3A, the reciprocal-locking means 25a and 25b are brought to cooperate with one another sequentially to a sliding movement for drawing together the two cross-sections 3a and 3b in a transverse direction, leading to the interlocking with force of the two cross-sections 3a and 3b, with the teeth 25a and 25b becoming engaged mutually in an irreversible way.

The passage for cutting into sections 22 empties onto the outside surface of the pinching closing device 1 for cutting into sections by at least one access, in this case an access slot 26 that can allow the introduction into the passage for cutting into sections 22 and the removal from the passage for cutting into sections 22, of the cutting element 2, by a transverse sliding movement or an element for control of the movement of the cutting element 2. On the other hand, the pinching passage 23 empties into the passage for cutting into sections 22.

In the embodiment of FIGS. 1 and 5, the passage for cutting into sections 22 goes through the slot 26 to an analogous diametrically opposed slot that is also located on the periphery of the pinching closing device 1 for cutting into sections. In another embodiment, not shown, the passage for cutting into sections 22 does not go through or is blind, not emptying into the diametrically opposed periphery of the pinching closing device 1 for cutting into sections, in which case there is only a single slot 26.

When two diametrically opposed slots are provided, it is possible, according to the embodiments, to provide a single cutting element 2 (or element for control of the movement of the cutting element 2) or two opposite cutting elements 2 (or control elements), each being introduced by a dedicated slot.

The passage for cutting into sections 22 also empties into—and interferes with—the space or separation 23a that is located between the two positive pinching closing sections 23a.

The access 26, arranged transversely, like the passage for cutting into sections 22, comprises a large side or length and a small side or width. The large side extends transversely to the right of the opening of the cradle of the surface 13 of the first indentation 11a, and it has a length that is at least slightly larger than this opening. With this constructive arrangement, it is ensured that the cutting element 2 will really interfere with the entire transverse cross-section of the tube T that is held in place pinched and closed in the two positive pinching closing segments 23a and that goes through the space or separation 23b that is located between them. And thus the cutting element 2 can transversely cut into sections the tube T in the space or separation 23b.

For this purpose, the combination means 24a, 24b of the cross-sections 3 are spaced from the surface 13 in such a way as to allow the passage of the cutting element 2 between the combination means 24a, 24b, without cutting them or even hardly touching them.

The small side of the access 26 is arranged axially. Its small length is matched to the thickness of the cutting element 2 (or the element for control of the movement of the cutting element 2) in such a way as to allow the passage and the guiding of the cutting element 2 (or the control element) in the passage for cutting into sections 22, without the cutting element 2 cutting or even hardly touching the pinching closing device 1 for cutting into sections itself.

The passage for cutting into sections 22 and the access 26 are dimensioned based on the dimensions of the pinching closing device 1 for cutting into sections, the nature of the shape and the dimensions of the tube T, as well as dimensions of the cutting element 2 or the control element of the element of the cutting element 2, in such a way as to ensure an effective cutting into sections.

Of course, the degrees of play necessary for the movement of the cutting element are provided.

The pinching closing device 1 for cutting into sections that was just described is implemented as it is now described for the purpose of pinching and closing a tube T and—in combination with at least one cutting element 2, within the scope of a pinching closing unit for cutting into sections—for the purpose of transversely cutting the tube T.

There is a pinching closing device 1 for cutting into sections that is in, or is brought into, the open state and of which each cross-section 3a and 3b comprises its two parts 4a and 4b, and 5a and 5b that are combined thanks to combination means 24a and 24b.

There is the tube T that, in this situation, is continuous and normally shaped for allowing fluid to pass.

The tube T is positioned in the desired pinching region RP of the latter, in the female indentation 11a of the first male cross-section 3a (installation phase). For example, the first male cross-section 3a is arranged so that its surface 13 is rotated frontally toward the operator or is rotated to be within the view of the operator. In the embodiment of FIG. 1, the first male cross-section 3a is arranged approximately with the horizontal axis 6, its surface 13 rotated upward.

The second female cross-section 3b is brought opposite the first male cross-section 3a, whereby the surfaces 13 and 14 are rotated toward one another. In the embodiment of FIG. 1, the second female cross-section 3b is arranged above the first male cross-section 3a, approximately with the horizontal axis 6, its surface 14 rotated downward perpendicular to the surface 13.

By a relative movement of drawing together the first and second cross-sections 3a and 3b, and parts 4a and 4b, on the one hand, and 5a and 5b, on the other hand, in this case by a relative movement of transverse sliding, the pinching closing device 1 is passed through for cutting into sections (its cross-sections 3 and parts 4 and 5) from the prior open state to the subsequent closed state. In the embodiment of FIG. 1, this relative movement of transverse sliding is a vertical movement.

This closing movement is continued until the end of travel, whereas the tube T is positively pinched until being closed in its two positive pinching closing zones ZPF by the surfaces 13 and 14 that deform it and thus restrict it, given the geometric relation that exists between the tube T and the two positive pinching closing segments 23a of the passage 23 (pinching phase).

This closing movement is facilitated as a result of irreversible locking means 25a, 25b, i.e., nonreturn means.

By bringing the pinching closing device 1 for cutting into sections into the closed state, the reciprocal-locking means 25a and 25b are made to cooperate simultaneously to keep closed the two parts 4a and 5a, on the one hand, and 4b and 5b, on the other hand, of each pair of parts of the first and second cross-sections 3a and 3b, in the position where the tube T is pinched and closed.

The tube T is thus kept pinched and closed between the two cross-sections 3a and 3b of the pinching closing device 1 for cutting into sections.

As indicated, it is also desired to cut the tube T into sections in the pinching region RP so as to obtain a tube T that is cut into sections in two lengths, each of them pinched and closed at its end part that is cut into sections or, as indicated above, only one being pinched and closed, with the other being only held in place. For this purpose, there is at least one cutting element 2.

Whereas the pinching closing device 1 for cutting into sections is in the closed state around the tube T, in a phase for cutting into sections, the tube T is cut after its pinching and its closing have been carried out in the flattening zone ZA, in which the tube is not positively pinched but nevertheless flattened. According to the embodiments, the tube T is cut into sections immediately after or a certain time after its positive pinching closing has been implemented.

For this purpose, the cutting element 2 is brought opposite to the access 26 of the pinching closing device 1 for cutting into sections.

Then, by a relative movement of drawing together the cutting element 2 and the pinching closing device 1 for cutting into sections, in this case a transverse sliding movement of the cutting element 2 in its own plane, the cutting element 2 is introduced via its end into the access 26, and the movement is continued until the cutting element 2 further penetrates into the passage for cutting into sections 22, and then into the space or separation 23b where it interferes with the tube T in its flattening zone ZA between the pairs of proximal surfaces 20a, 21a and 20b, 21b. It is thus that the tube T is cut or cut into sections transversely.

In this movement, the cutting element 2 is, if necessary, guided by the pairs of proximal surfaces 20a, 21a and 20b, 21b, and also, if necessary, by the combination elements 24a, 24b.

Thus, the tube T is cut into sections without the cutting element 2 cutting into sections, penetrating into or interfering frontally with the pinching closing device 1 for cutting into sections. As a result, the appearance of troublesome chips or waste that originates from the pinching closing device 1 for cutting into sections is avoided.

According to the embodiments, the sliding movement of the cutting element 2 is continued on either side of the pinching closing device 1 for cutting into sections if the passage for cutting into sections 22 goes through or is stopped in the suitable position if the passage for cutting into sections 22 does not go through and is blind. According to the embodiments, the cut is made by means of a single cutting element 2 or two opposite cutting elements 2.

Figure 9:
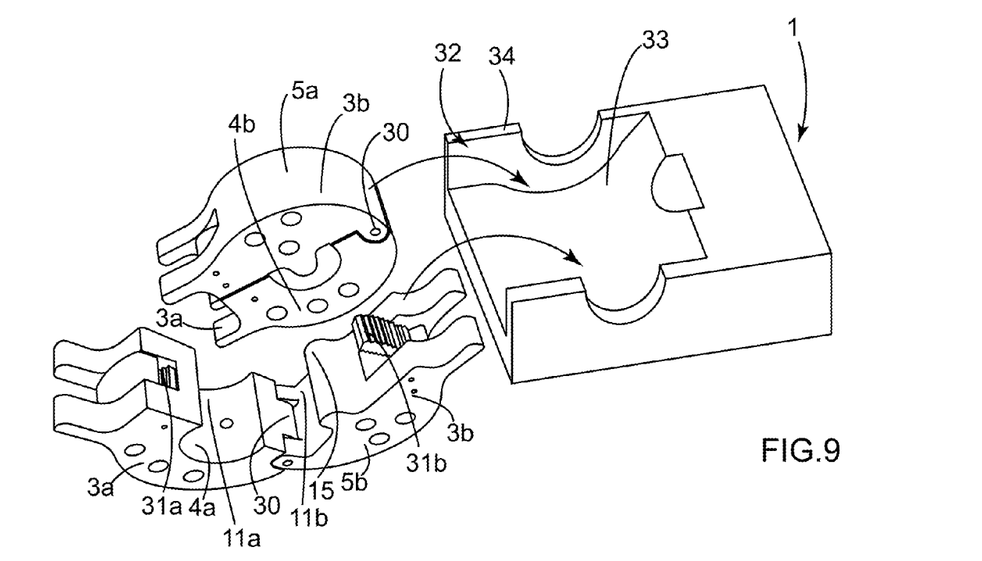
FIGS. 9 and 10 are two perspective views of a second possible embodiment family of a pinching closing unit for cutting into sections.

According to the embodiments, the cutting element 2 is passed into the passage for cutting into sections 22 without contact with the pinching closing device 1 for cutting into sections (FIG. 2) or on the contrary with a surface contact that slides with the pinching closing device 1 for cutting into sections (FIG. 9).

Once the tube T is cut into sections in its flattening zone ZA, the cutting element 2 can be removed either because it passed through on either side of the pinching closing device 1 for cutting into sections if the passage for cutting into sections 22 goes through, or by a sliding movement in the direction opposite to the direction of introduction if the passage for cutting into sections 22 does not go through and is blind.

In this situation, it is then possible to dissociate the parts 4a and 4b, on the one hand, and the parts 5a and 5b, on the other hand, by dissociating from one another the combination means 24a and 24b by an axial sliding movement of separation (dissociation phase). However, the parts 4a and 5a, on the one hand, and 4b and 5b, on the other hand, are left attached to the end parts of tube T that are cut into sections by pinching them and closing them.

Then, a tube T is obtained that is cut into sections of two segments or lengths, each pinched and closed at its end part that is cut into sections, to which are attached for this purpose one pair of parts, respectively 4a and 5a, on the one hand, and 4b and 5b, on the other hand.

Or, as indicated, a tube T is obtained that is cut into sections of two segments or lengths, which is pinched and closed on one side.

According to a variant embodiment, the pinching passage 23 has an adjustable opening for adapting to tubes T of different geometries, in particular sizes.

For this purpose, it can be provided in one embodiment to use different devices 1 that correspond to different geometries, in particular sizes, which makes it possible to cover a wide spectrum of geometries of tubes T.

In another embodiment (FIG. 3), it is provided that the relative movement of drawing together and closing the first and second cross-sections 3a and 3b is more or less large, in such a way that the pinching passage 23 is respectively more or less small. This is made possible as a result of the existence of reciprocal-locking means 25a and 25b, comprising a series of stepped contoured hooking teeth between the core 7a, 7b of the cross-section 3a, 3b and the free border of the edge of the adjacent lip 8a, 8b; this makes possible different relative positions for locking cross-sections 3a and 3b by a nonreturn.

In one embodiment (FIG. 4), it is provided that one and/or the other of the two indentations 11a and 11b is slightly inclined along the axis 6, toward the free border of the edge of the lip 8a, 8b and toward the proximal end 20a, 20b, 21a, 21b.

This constructive arrangement makes it possible to exert a more significant pinching of the tube T toward this proximal end 20a, 20b, 21a, 21b, which is such that it expels the fluid found in the tube T toward the other distal end 19.

According to one embodiment (FIG. 6), the combination means 24a and 24b comprise a projection 24a and a groove 24b, made on the end surfaces and proximal surfaces 20a, 20b, 21a, 21b, and extend in a non-parallel manner to the axis 6 as in the embodiment of FIGS. 1 and 5, but extend transversely. In this case, the combination or dissociation movement is a transverse sliding movement parallel to the direction of the projection 24a and the groove 24b and not an axial movement.

According to another embodiment (FIG. 7), the combination means 27 differ from the projection combination means 24a and hole or groove 24b, as described above, and comprise a removable connecting part in the form of a clip 27, able to combine in a removable way the two parts 4a and 4b or 5a and 5b in a way that is not direct but indirect.

This clip 27 comprises a flat core 28, able to come, when the clip is mounted in a combination situation, against the outside surface of the pinching closing device 1 for cutting into sections. This core 28 is pierced by a slot 26a that can come perpendicular to the access 26 and can superpose itself on it.

From the core 28, four (or more) projections that are in rod form 29a, contoured, parallel to one another and orthogonal to the core 28 are adjacent. These projections 29a are able to work with an equal number of transverse grooves 29b made on the outside surface of the pinching closing device 1 for cutting into sections on each part 4a, 4b, 5a and 5b.

In the different embodiments described above, the two parts 4a and 5a, on the one hand, and 4b and 5b, on the other hand, of the two cross-sections 3a and 3b are separate parts and the relative closing movement is a transverse sliding movement in translation.

In another embodiment (FIGS. 9 and 10), the two parts 4a and 5a, on the one hand, and 4b and 5b, on the other hand, of the two cross-sections 3a and 3b are parts that are not separate but combined structurally with one another to pivot around a pivoting axis 30 that is parallel to the axis 6, and the relative closing movement is not a transverse sliding movement in translation but a pivoting movement around the pivoting axis 30. The pivoting axis 30 is offset very broadly relative to the axis 6, on a longitudinal side of the pinching closing device 1 for cutting into sections, in such a way that—the pivoting radius being large—the end of the interlocking pivoting movement differs little from a transverse sliding, as above.

Figure 10:
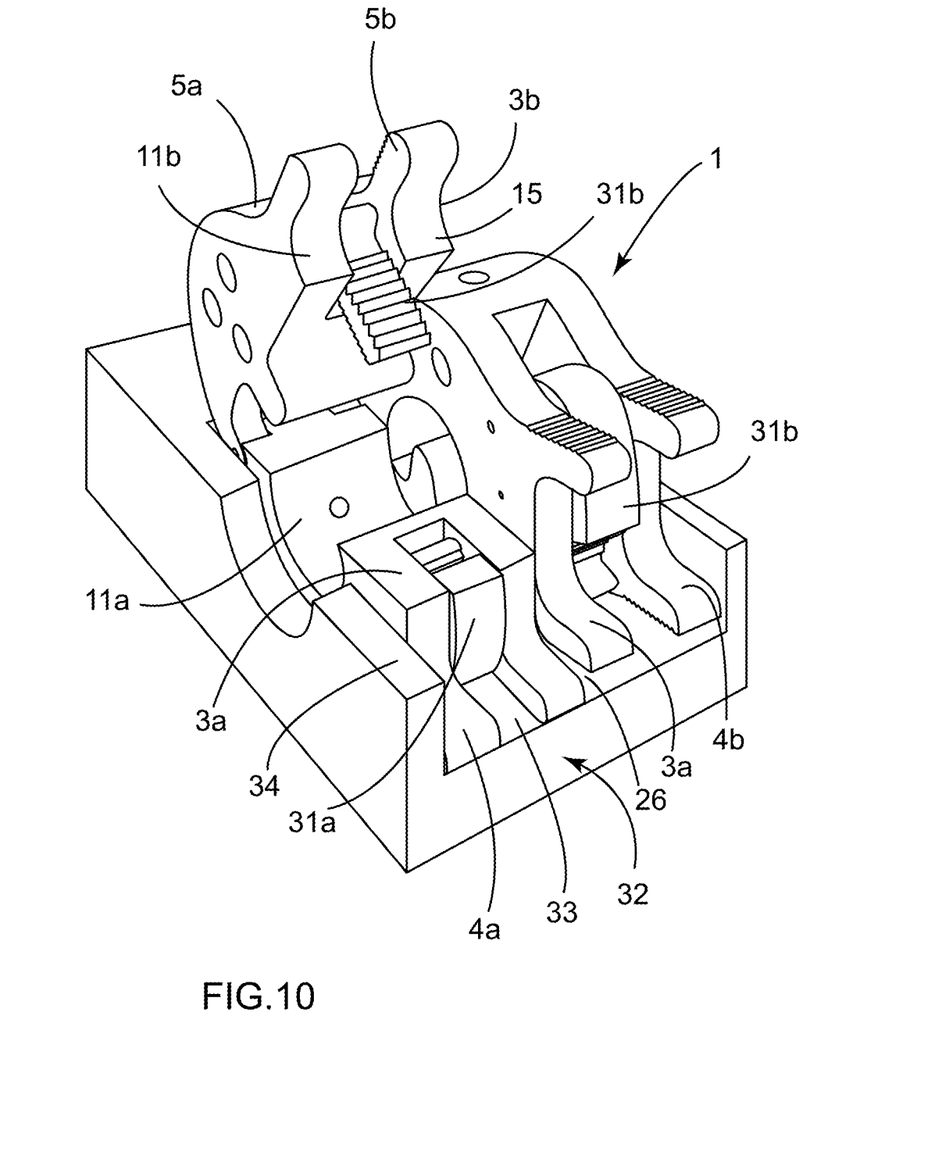

From the longitudinal side opposite the axis 6, there are provided locking means 25a and 25b, one of which comprises a female part 31a, connected to one of the parts 4a, 5a or 4b, 5b, and equipped with teeth 25a, and the other of which comprises a male part 31b, connected to the other part 5a, 4a or 5b, 4b, and equipped with teeth 25b.

The teeth 25a, 25b, as above, are contoured irreversible hooking teeth, oriented in two opposite directions, extending axially.

In the embodiment of FIGS. 9 and 10, as in the embodiment of FIG. 7, the combination means 32 comprise, in line with the part 27, a removable connecting part in the shape of a cradle 32, able to combine in a removable way the two parts 4a and 4b or 5a and 5b in a way that is not direct but indirect.

This part 32 comprises a cradle 33, able to come, when the part 32 is mounted in a combination situation, against the outside surface of the pinching closing device 1 for cutting into sections, on one side of the latter, in such a way as to leave the other side free or the passage for cutting into sections 22 is accessible.

The cradle 33 comprises two lips 34 that face one another, able to encircle the parts 4a and 4b or 5a and 5b by their distal end surfaces 19.

In the embodiments described above, the pinching closing device 1 for cutting into sections structurally does not include the at least one cutting element 2, with the latter, however, being combined functionally.

According to other embodiments, the pinching closing device 1 for cutting into sections structurally and functionally includes at least one cutting element 2. For example, in the case of FIG. 8, the cutting element 2 forms a sort of guillotine that has a general elevated U shape and is mounted to slide in its own plane on the proximal end surface 20a or 20b of one of the parts 4a, 4b that is equipped with suitable guiding means. In this embodiment, there is provided a single cutting element 2 or two cutting elements on the two end surfaces 20a and 20b. In this embodiment, the access 26 allows the passage of an element for control of the movement of the cutting element 2, such as a type of blade.

The invention claimed is:

1. Process for cutting into sections and closing a flexible tube, comprising:
    using a pinching closing unit that cuts a flexible tube, the pinching closing unit comprising a pinching closing device (1) and at least one cutting element (2) with a frontal cutting edge,
    whereby the pinching closing device (1) comprises two cross-sections (3a, 3b), each of the two cross-sections having two hollow parts (4a, 4b and 5a, 5b), the two cross-sections (3a, 3b) being a first cross-section (3a) and a second cross-section (3b), at least one pair of the hollow parts (4a and 5a or 4b and 5b) having two indentations (11a, 11b), wherein a first of the two indentations (11b) is a female indentation and a second of the two indentations is a male indentation (11a),
    using combination means (24a, 24b, 27, 32) to place the hollow parts (4a, 4b and 5a, 5b) of each of the two cross-sections (3a, 3b) into an extension of one another and thereby making between the hollow parts of each of the two cross-sections (3a, 3b) a transverse passage for cutting (22), the transverse passage (22) having an access (26) for the at least one cutting element (2),
    wherein the pinching closing device (1) has i) an open state where the two cross-sections (3a, 3b) are separated from one another, and ii) a closed state where the two cross-sections (3a, 3b) are drawn together and closed on one another and kept closed by locking means (25a, 25b),
    wherein in the closed state, a surface (13, 14) of the two indentations (11a, 11b) form a positive pinching closing passage (23) for pinching and closing the tube, the positive pinching closing passage (23) being limited by the surface[s] (13, 14) of the two indentations (11a, 11b) and having, in transverse straight cross-section, a general U shape,
    wherein the at least one cutting element (2) has a shape and dimension[s] such that the at least one cutting element, via the access (26), passes into the transverse passage (22) and thus cuts the tube with the tube being pinched and closed by the pinching closing device (1),
    with the pinching closing device (1) in the open state, positioning a pinching region of the tube in the first indentation (11b) of the first cross-section (3a), and bringing the second cross-section (3b) opposite the first cross-section, then drawing the first and second cross-sections (3a, 3b) together and closing the first and second cross-sections (3a, 3b) on one another to bring the pinching closing device (1) into the closed state, and, with cooperation of the locking means (25a, 25b), closing the first and second cross-sections (3a, 3b) on one another until the tube is positively pinched and closed in at least one positive pinching closing zone by the surface (13, 14) of the two indentations, whereby the tube is held in place thus pinched and closed between the two cross-sections (3a, 3b),
    with the pinching closing device (1) in the closed state and using the at least one cutting element (2), cutting the tube at a location between the hollow parts (4a and 5a, 4b and 5b),
    wherein in said cutting step, a frontal cutting edge of the at least one cutting element (2) passes into the transverse passage (22) and cuts the tube into the two sections without the frontal cutting edge making contact with the pinching closing device (1), after said cutting step, dissociating the combination means (24a, 24b) from the hollow parts (4a and 4b, 5a and 5b) of each of the two cross-sections (3a, 3b), wherein the at least one pair of the hollow parts (4a and 5a or 4b and 5b) having the two indentations (11a, 11b) remains attached to an end part of the tube that has been cut, and wherein the at least one cutting element (2) is accessible from outside of the pinching closing device when the pinching closing device is clamped on the tube.

2. Process according to claim 1, wherein the at least one cutting element (2) is passed into the transverse passage (22) either i) without any contact with the pinching closing device (1) or ii) with a side surface contact of the at least one cutting element (2) that slides in the pinching closing device (1).

3. Process according to claim 1, wherein the at least one cutting element (2), is a single cutting element (2) or two opposite cutting elements (2).

4. Process according to claim 1, wherein the tube is cut in a flattening zone in which the tube is not positively pinched.

5. Process according to claim 1, wherein the second cross-section (3b) is brought opposite the first cross-section (3a) and the pinching closing device (1) is brought into the closed state, by a relative movement of transverse translation or pivoting around an axis (30) that, relative to a longitudinal axis (6) of the pinching closing device (1), is offset on a longitudinal side of the pinching closing device (1).

6. Process according to claim 1, wherein in dissociating step, each pair[s] of the hollow parts (4a, 5a and 4b, 5b) remain attached to respective end parts of the tube that has been cut.

7. Process according to claim 1, wherein the at least one positive pinching closing zone corresponds to a zone of two lateral folds of the tube.

8. Pinching closing unit for cutting into sections (1+2) for implementation of the process according to claim 1, comprising:

the pinching closing device (1) that comprises the two cross-sections (3a, 3b), each of the two cross-section having the hollow parts (4a, 4b, and 5a, 5b), the at least one pair of the hollow parts (4a and 5a or 4b and 5b) having the two indentations (11a, 11b), whereby the hollow parts (4a, 4b, and 5a, 5b) can be placed in the extension of one another in a removable way by the combination means (24a, 24b, 27, 32) while making between the hollow parts the transverse passage (22) that has the access (26) whereby the transverse passage (22) is made between two pairs of transverse end surfaces and proximal surfaces (20a, 20b, 21a, 21b) of the two cross-sections (3a, 3b), located opposite one another and offset close to one another along the axis (6) of the pinching closing device (1), which are movable between i) the open state where the two cross-sections (3a, 3b) are separated from one another, and ii) the closed state where the two cross-sections are drawn together and closed on one another and kept closed by the locking means (25a, 25b) and where the surfaces (13, 14) of the two indentations (11a, 11b) form the passage (23) for pinching and closing the tube, comprising at least one segment (23a) to which the space (23b) is axially adjacent, in which space the passage (22) empties and where the tube is held in place, and flattened to a certain degree, with one of the two indentations (11b) being the female indentation, and with another of the two indentations being the male indentation (11a), the two indentations (11a, 11b), in the closed state of the pinching closing device (1) making between the two sections the positive pinching closing passage (23) that is limited by the surface[s] (13, 14) of the two indentations (11a, 11b), having, in the transverse straight cross-section, the general U shape, and the at least one cutting element (2) having the frontal cutting edge and a shape and dimension selected such that the at least one cutting element, via the access, passes into the transverse passage of the pinching closing device and thus cuts the tube, wherein the frontal cutting edge of the at least one cutting element (2) passes into the transverse passage (22) and cuts the tube without the frontal cutting edge making contact with the pinching closing device (1), and wherein the at least one cutting element (2) is accessible from the outside of the pinching closing device when the pinching closing device is clamped on the tube.

9. Pinching closing unit for cutting into sections (1+2) according to claim 8, wherein the first of the two indentations (11b) is the female indentation, and the second of the two indentations is the male indentation (11a), whereby the two indentations (11a, 11b), in the closed state of the pinching closing device (1) make therebetween the positive pinching closing passage (23) that is limited by the surface[s] (13, 14) of the indentations (11a, 11b), having, in the transverse straight cross-section, the general U shape.

10. Pinching closing unit for cutting into sections (1+2) according to claim 8, wherein a width of an opening of the positive pinching closing passage (23), defined by the transverse spacing between the surfaces (13 and 14) of the transverse straight cross-section in the general U shape, is smaller than twice a thickness of a wall of the tube to be pinched.

11. Pinching closing unit for cutting into sections (1+2) according to claim 8, wherein the hollow parts (4a, 4b and 5a, 5b) of each cross-section (3a and 3b) are either
i) analogous, with the pinching closing device (1) ensuring a closing function of the tube on the tube in two positive pinching closing zones, or
ii) different, with the pinching closing device (1) ensuring a function of the tube on the tube in a single positive pinching closing zone and being only held in place in another other zone.

12. Pinching closing unit for cutting into sections (1+2) according to claim 8, wherein the locking means (25a and 25b) are either
i) irreversible for the two pairs of the hollow parts (4a and 5a, 4b and 5b) or
ii) irreversible for one of the pairs of the hollow parts (4a and 5a or 4b and 5b) and reversible for another of the pairs of the hollow parts (4b and 5b or 4a and 5a).

13. Pinching closing unit for cutting into sections (1+2) according to claim 8, wherein the positive pinching closing passage (23) has an adjustable opening, with the relative movement for bringing the second cross-section (3b) opposite the first cross-section (3a) and the pinching closing device (1) in the closed state being large so that the positive pinching closing passage (23) is respectively small.

14. Pinching closing unit for cutting into sections (1+2) according to claim 8, wherein either the two indentations (11a and 11b) i) have the same shape, the same arrangement and the same dimension[s], constant and uniform, from one free end to a next free end, or ii) one indentation and/or another indentation of the two indentations (11a, 11b) is inclined along the axis (6) of the pinching closing device (1), toward a free border of an edge of a lip (8a, 8b) and toward a proximal end (20a, 20b, 21a, 21b) for exerting a more significant pinching of the tube toward the proximal end (20a, 20b, 21a, 21b) and expelling a fluid that is found in the tube toward a distal end (19).

15. Pinching closing unit for cutting into sections (1+2) according to claim 8, further comprising separation means that consist of stops made on the two ends of the transverse surfaces and proximal surfaces (20a, 20b, 21a, 21b) of the two cross-sections.

16. Pinching closing unit for cutting into sections (1+2) according to claim 8 wherein the combination means (24a, 24b, 27, 32) comprise at least one projection (24a) made on one of the hollow parts (4a, 4b, 5a, 5b) of one of the two cross-sections, able to work in a removable way with at least one blind hole or hollow or groove (24b) that is complementary, made on another of the hollow parts of one cross-section (3a, 3b), and a projection (24a) and a hole or groove (24b) extending parallel to the axis (6) or transversely.

17. Pinching closing unit for cutting into sections (1+2) according to claim 8, wherein either the combination means comprise i) at least one removable connecting part in the form of a clip (27), able to combine the hollow parts (4a and 4b or 5a and 5b) in a removable way and in an indirect way, with the clip (27) comprising a core (28) from which four projections that are in rod form (29a) and that are able to work with four transverse grooves (29b) made on the outside surface of the pinching closing device (1) are adjacent, on each hollow part (4a, 4b, 5a, 5b), or ii) a removable connecting part in the shape of a cradle (32), able to combine the hollow parts (4a and 4b or 5a and 5b) in a removable way and an indirect way; the cradle (33) comprises two lips (34) that face one another, able to encircle the hollow parts (4a and 4b or 5a and 5b) by distal end surfaces (19) thereof.

18. Pinching closing unit for cutting into sections (1+2) according to claim 8, wherein the two cross-sections (3a and 3b) are two separate hollow parts and are brought to the closed state by a relative transverse sliding movement, whereby one cross-section (3a) of the two cross-sections (3a and 3b) is a male cross-section and the other cross-section (3b) is a female cross-section, with the male cross-section (3a) comprising and being limited on the outside by a first core (7a) and two first lips (8a), and with the female cross-section (3b) comprising and being limited on the outside by a second core (7a) and two second lips (8b).

19. Pinching closing unit for cutting into sections (1+2) according to claim 18, wherein a separation between the two opposite outside surfaces (9) of the first two lips (8a) corresponds to a separation between two inside surfaces (10) opposite the second two lips (8b), in such a way as to allow, in the closed state of the pinching closing device (1), the interlocking with adjustment of the two cross-sections (3a and 3b), with two opposite of outside surfaces (9) then being in contact and supported on the two inside surfaces (10).

20. Pinching closing unit for cutting into sections (1+2) according to claim 8, wherein the two cross-sections (3a and 3b) are hollow parts that are structurally combined with one another in pivoting around an axis (30) that, relative to a longitudinal axis (6) of the pinching closing device (1), is offset on a longitudinal side of the pinching closing device (1), with the two cross-sections (3a and 3b) being brought into the closed state by a relative pivoting movement around a pivoting axis (30).

21. Pinching closing unit for cutting into sections (1+2) according to claim 8, wherein the two cross-sections (3a and 3b) have the same axial length.

* * * * *